US006433243B1

(12) United States Patent
Woltman et al.

(10) Patent No.: US 6,433,243 B1
(45) Date of Patent: Aug. 13, 2002

(54) WATER PERMEABLE POROUS LAYER MATERIALS TREATED WITH SURFACTANT-MODIFIED CYCLODEXTRINS

(75) Inventors: Garry Roland Woltman, Greenville, WI (US); Yuelong Liu, Alpharetta; Roger Bradshaw Quincy, III, Cumming, both of GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/472,719

(22) Filed: Dec. 28, 1999

Related U.S. Application Data

(60) Provisional application No. 60/121,934, filed on Feb. 26, 1999.

(51) Int. Cl.$^7$ .............................. A61F 13/15; A61L 9/00
(52) U.S. Cl. .................. 604/359; 424/76.21; 424/76.6; 424/443; 514/58
(58) Field of Search .................................. 604/359, 360, 604/367; 424/76.1, 76.2, 76.21, 76.5, 76.6, 401, 402, 443; 514/58

(56) References Cited

U.S. PATENT DOCUMENTS

| | | | |
|---|---|---|---|
| 3,338,992 A | 8/1967 | Kinney | 264/24 |
| 3,341,394 A | 9/1967 | Kinney | 161/72 |
| 3,485,706 A | 12/1969 | Evans | 161/72 |
| 3,502,538 A | 3/1970 | Petersen | 161/150 |
| 3,502,763 A | 3/1970 | Hartmann | 264/210 |
| 3,534,075 A | 10/1970 | Andress, Jr. | 260/404.5 |
| 3,542,615 A | 11/1970 | Dobo et al. | 156/181 |
| 3,692,618 A | 9/1972 | Dorschner et al. | 161/72 |
| 3,802,817 A | 4/1974 | Matsuki et al. | 425/66 |
| 3,849,241 A | 11/1974 | Butin et al. | 161/169 |
| 3,855,046 A | 12/1974 | Hansen et al. | 161/150 |
| 3,901,236 A | 8/1975 | Assarsson et al. | 128/284 |
| 3,903,259 A | 9/1975 | Hart | 424/76 |
| 3,920,020 A | 11/1975 | Kraskin | 128/290 |
| 4,015,050 A | 3/1977 | Birchall et al. | 428/480 |
| 4,076,663 A | 2/1978 | Masuda et al. | 260/17.4 GC |
| 4,100,324 A | 7/1978 | Anderson et al. | 428/288 |
| 4,273,786 A | 6/1981 | Kraskin | 424/319 |
| 4,286,082 A | 8/1981 | Tsubakimoto et al. | 526/240 |
| 4,300,561 A | 11/1981 | Kaczmarzyk et al. | 128/285 |
| 4,340,563 A | 7/1982 | Appel et al. | 264/518 |
| 4,356,190 A | 10/1982 | Kraskin | 424/319 |
| 4,377,167 A | 3/1983 | Kaczmarzyk et al. | 128/285 |
| 4,425,130 A | 1/1984 | DesMarais | 604/389 |
| 4,617,230 A | 10/1986 | Shah et al. | 428/288 |
| 4,638,058 A | 1/1987 | Brandt et al. | 536/103 |
| 4,818,464 A | 4/1989 | Lau | 264/510 |
| 4,929,378 A | 5/1990 | Morita et al. | 252/105 |
| 5,108,820 A | 4/1992 | Kaneko et al. | 428/198 |
| 5,161,686 A | 11/1992 | Weber et al. | 206/440 |
| 5,336,552 A | 8/1994 | Strack et al. | 428/224 |
| 5,348,667 A | * 9/1994 | Bacon et al. | 252/8.6 |
| 5,382,400 A | 1/1995 | Pike et al. | 264/168 |
| 5,429,528 A | 7/1995 | Trinh et al. | 604/359 |
| 5,445,747 A | 8/1995 | Kvietok et al. | 252/86 |
| 5,533,990 A | 7/1996 | Yeo | 604/363 |
| 5,534,165 A | 7/1996 | Pilosof et al. | 252/8.91 |
| 5,571,782 A | 11/1996 | Trinh et al. | 512/4 |
| 5,578,563 A | 11/1996 | Trinh et al. | 510/513 |
| 5,591,146 A | 1/1997 | Hasse | 604/359 |
| 5,593,670 A | 1/1997 | Trinh et al. | 424/76.1 |
| 5,594,125 A | 1/1997 | Seyschab et al. | 536/103 |
| 5,648,067 A | 7/1997 | Dillenburg et al. | 424/65 |
| 5,663,134 A | 9/1997 | Trinh et al. | 510/406 |
| 5,668,097 A | 9/1997 | Trinh et al. | 510/293 |
| 5,670,475 A | 9/1997 | Trinh et al. | 510/470 |
| 5,685,872 A | 11/1997 | Syverson | 604/360 |
| 5,690,919 A | 11/1997 | Röckl et al. | 424/65 |
| 5,698,476 A | * 12/1997 | Johnson et al. | 442/121 |
| 5,714,137 A | 2/1998 | Trinh et al. | 424/76.4 |
| 5,714,445 A | 2/1998 | Trinh et al. | 510/103 |
| 5,718,887 A | 2/1998 | Wolf et al. | 424/65 |
| 5,733,272 A | 3/1998 | Brunner et al. | 604/359 |
| 5,738,860 A | 4/1998 | Schonfeldt et al. | 424/402 |
| H1732 H | 6/1998 | Johnson | 428/68 |
| 5,769,833 A | 6/1998 | Hasse | 604/359 |
| 5,780,020 A | 7/1998 | Peterson et al. | 424/65 |
| 5,785,697 A | * 7/1998 | Trombetta et al. | 604/378 |
| 5,821,215 A | 10/1998 | Crudden et al. | 510/392 |
| 5,849,325 A | 12/1998 | Heinecke et al. | 424/443 |
| 5,860,959 A | 1/1999 | Gent | 604/332 |

(List continued on next page.)

FOREIGN PATENT DOCUMENTS

| | | | |
|---|---|---|---|
| EP | 392 607 | 10/1990 | C11D/17/04 |
| EP | 392 608 | 10/1990 | C08B/37/16 |
| EP | 0 510 619 A1 | 4/1992 | |
| EP | 510 619 | 10/1992 | A61F/13/15 |
| EP | 562 620 | 9/1993 | A61L/15/46 |
| EP | 0 562 620 A1 | 9/1993 | |

(List continued on next page.)

OTHER PUBLICATIONS

Dharmawardana, Udeni R., et al.: *A Surface Tension Method for Determining Binding Constants for Cyclodextrin Inclusion Complexes of Ionic Surfactants*, Langmuir, vol. 9, No. 9, 2258–2263, 1993.

U. Denter et al.: *Verfahrenstechnische Methoden zur permanenten Fixierung von Cyclodestrinderivaten auf textilen Oberflächen*, Textilveredlung, 33–39, vol. 32, No. 1/2, 1997.

*Primary Examiner*—John G. Weiss
*Assistant Examiner*—Michael Bogart
(74) *Attorney, Agent, or Firm*—Pauley Petersen Kinne & Erickson

(57) ABSTRACT

A thermoplastic porous water-permeable layer material has at least one odor-reducing surface which is wettable to aqueous liquids and capable of controlling a wide variety of malodors. The thermoplastic water-permeable layer material is treated with a surfactant-modified cyclodextrin prepared by mixing or chemically reacting a cyclodextrin-based odor absorbing material with a surfactant-producing compound. The layer material thus treated can be used in a wide variety of personal care and medical absorbent products, as well as other applications.

43 Claims, No Drawings

U.S. PATENT DOCUMENTS

| | | | | |
|---|---|---|---|---|
| 5,865,792 A | * | 2/1999 | Ledger et al. | 604/20 |
| 5,871,718 A | * | 2/1999 | Lucas et al. | 424/65 |
| 5,871,719 A | * | 2/1999 | Lucas et al. | 424/65 |
| 5,874,067 A | | 2/1999 | Lucas et al. | 424/65 |
| 5,928,631 A | * | 7/1999 | Lucas et al. | 424/65 |
| 5,932,495 A | | 8/1999 | Boney et al. | 442/121 |
| 5,942,217 A | * | 8/1999 | Woo et al. | 424/76.1 |
| 5,955,093 A | * | 9/1999 | Woo et al. | 424/401 |
| 5,968,404 A | * | 10/1999 | Trinh et al. | 252/8.91 |
| 5,997,759 A | * | 12/1999 | Trinh et al. | 252/8.91 |
| 6,001,343 A | * | 12/1999 | Trinh et al. | 424/76.4 |
| 6,021,822 A | | 2/2000 | Izawa et al. | 141/110 |
| 6,028,016 A | | 2/2000 | Yahiaoui et al. | 442/118 |
| 6,031,147 A | | 2/2000 | Gross | 604/359 |
| 6,033,486 A | * | 3/2000 | Andros | 134/6 |
| 6,033,679 A | * | 3/2000 | Woo et al. | 424/401 |
| 6,066,673 A | | 5/2000 | McIver et al. | 514/634 |
| 6,100,233 A | * | 7/2000 | Sivik et al. | 512/26 |
| 6,106,738 A | | 8/2000 | Woo et al. | 252/8.91 |
| 6,229,062 B1 | * | 5/2001 | Mandell et al. | 604/367 |
| 6,284,231 B1 | * | 9/2001 | Trinh et al. | 424/76.1 |
| 6,296,936 B1 | | 10/2001 | Yahiaoui et al. | 428/378 |

FOREIGN PATENT DOCUMENTS

| | | | | |
|---|---|---|---|---|
| EP | 685 213 | | 12/1995 | A61F/13/15 |
| EP | 811 390 | | 12/1997 | A61L/15/46 |
| EP | 811 391 | | 12/1997 | A61L/15/46 |
| EP | 813 848 | | 12/1997 | A61F/13/15 |
| EP | 894 502 | | 2/1999 | A61L/15/18 |
| GB | 1 517 042 | | 5/1975 | |
| WO | 94 22500 | | 10/1994 | A61L/15/46 |
| WO | WO 95/17175 | * | 6/1995 | A61K/9/70 |
| WO | 96 04937 | | 2/1996 | A61L/9/01 |
| WO | 96 05358 | | 2/1996 | D06M/15/11 |
| WO | 96/24318 | | 8/1996 | A61F/13/15 |
| WO | WO 9/31698 | | 9/1997 | |
| WO | 98 07455 | | 2/1998 | A61L/9/01 |
| WO | 98 17239 | | 4/1998 | A61K/7/32 |
| WO | 98 17240 | | 4/1998 | A61K/7/32 |
| WO | 98 18439 | | 5/1998 | A61K/7/32 |
| WO | WO 98/20916 | | 5/1998 | |
| WO | 98 25808 | | 6/1998 | A61L/9/01 |
| WO | 98/56342 | | 12/1998 | A61K/7/48 |
| WO | 99/45973 | | 9/1999 | A61L/15/44 |
| WO | 99/45974 | | 9/1999 | A61L/15/44 |
| WO | 00/10500 | | 3/2000 | A61F/13/15 |

\* cited by examiner

WATER PERMEABLE POROUS LAYER MATERIALS TREATED WITH SURFACTANT-MODIFIED CYCLODEXTRINS

This application claims priority from Provisional application Ser. No. 60/121,934, filed Feb. 26, 1999.

FIELD OF THE INVENTION

This invention relates to chemical compounds and blends which control odor and impart surface wetting properties to water-permeable porous layer materials. In particular, the invention relates to water-permeable porous layer materials treated with these dual purpose chemical compounds and blends.

BACKGROUND OF THE INVENTION

Water-permeable nonwoven fabrics, porous films, open-celled foams, and other layer materials and their manufacture have been the subject of extensive development resulting in a wide variety of materials for numerous applications. For example, nonwovens of light basis weight and open structure are used in personal care items such as disposable diapers as liner fabrics that provide dry skin contact but readily transmit fluids to more absorbent materials which may also be nonwovens of a different composition and/or structure. Nonwovens of heavier weights may be designed with pore structures making them suitable for filtration, absorbent and barrier applications such as wrappers for items to be sterilized, wipers or protective garments for medical, veterinary or industrial uses. Even heavier weight nonwovens have been developed for recreational, agricultural and construction uses. Water-permeable porous thermoplastic films are also employed in some of these applications, and may be combined with nonwoven webs. Open-celled foams are also useful in some applications.

It is not always possible to efficiently produce a porous, water-permeable layer material having all the desired properties as formed, and it is frequently necessary to treat the material with a surfactant to improve or alter surface properties such as wettability by one or more fluids, repellency to one or more fluids, electrostatic characteristics, conductivity, and softness, to name just a few examples. Conventional surfactant treatments involve steps such as dipping the substrate in a treatment bath, coating or spraying the substrate with the treatment composition, and printing the substrate with the treatment composition. For cost and other reasons it is usually desired to use the minimum amount of treatment composition that will produce the desired effect with an acceptable degree of uniformity.

For many thermoplastic layer material end use applications, it is desirable to reduce, prevent, or eliminate odors. For diapers and other incontinence products, it is desirable to reduce or eliminate the odor of ammonia which is present in urine. For feminine hygiene products, it is desirable to reduce or eliminate the odor of triethylamine. Other common odor-producing substances include isovaleric acid, dimethyl disulfide, and dimethyl trisulfide.

Odor control agents include odor inhibitors, odor absorbers, and other compounds which reduce, prevent, or eliminate odors. Odor inhibitors prevent the odor from forming. For example, U.S. Pat. No. 4,273,786 to Kraskin teaches the use of an aminopolycarboxylic acid compound for inhibiting the formation of ammonia from urea in urine. Odor absorbers and adsorbers remove odor after it is formed. Examples of odor control agents that remove odor by absorption or adsorption include activated carbon, silica, and cyclodextrins.

Typical odor control agents based on cyclodextrins cannot easily be applied from aqueous solutions to water-permeable thermoplastic substrates such as polyolefin nonwoven fabrics, porous films, and open-celled foams because the surface tension of these solutions is too high to wet out the hydrophobic substrate. Personal care products such as diapers and feminine care pads typically contain polyolefin nonwoven fabrics and/or other porous thermoplastic cover layers. Therefore, typical odor control agents cannot usually be applied to the porous thermoplastic components of personal care products. Instead, these odor control agents are usually introduced as powders to the product, which has several drawbacks. For example, placement and containment of the powder in the product can be troublesome. More importantly, powders do not present optimum surface area for odor absorption due to a rather low surface to volume ratio. Therefore, more odor control agent will be needed if in powder form.

There is a need or desire for odor absorbing compounds and blends which can be applied to a water-permeable hydrophobic (e.g., thermoplastic) substrate in a liquid or solvent form, and which have enough surface wetting properties to facilitate even fluid distribution and durability.

SUMMARY OF THE INVENTION

The present invention is directed to a water-permeable porous layer material which has been treated with a surfactant-modified odor control agent. The surfactant-modified odor control agent can be prepared by blending a cyclodextrin-based odor control agent with a surfactant, or by chemically reacting a cyclodextrin-based odor control agent with a surfactant-producing compound. Surfactant-producing compounds include both surfactants, and other compounds which behave as surfactants following the chemical reaction. The surfactant-modified odor control agent can be applied to the water-permeable porous layer material using conventional internal or external application techniques for surfactants, and is preferably applied using an external application technique. The resulting treated substrate is more wettable to aqueous liquids, and absorbs odors at its surfaces.

The water-permeable porous layer material can be a hydrophobic material, made using one or more thermoplastic polymers. For instance, the porous substrate may be a thermoplastic nonwoven filament web, a porous thermoplastic film, an open-celled foam material, or a combination thereof. A thermoplastic nonwoven filament web is preferred. The treated, water-permeable porous layer material can be used in a wide variety of personal care products and medical products, and in other applications.

The surfactant-modified odor control agents can be applied to hydrophobic substrates (for example, polyolefin-based porous films, open-celled foam layers, and nonwoven webs) from an aqueous solution, because the surface tension of the solution is low enough to wet out the low surface energy substrate. For instance, coating the surfactant-modified odor control agent on the polyolefin fibers of a polyolefin nonwoven fabric will optimize the surface to volume ratio of odor control chemistry, and thus provides better odor control (e.g., odor absorption, adsorption or inhibition). Furthermore, fibers coated with a surfactant-modified odor control agent will be in direct contact with body fluids as the fluids enter and wick through the fabric components of the personal care product. This will provide optimum odor control since the odors are believed to emanate from the body fluids.

It is thus a feature and advantage of the invention to provide a treated water-permeable porous layer material having at least one surface which is more wettable to aqueous liquids than the untreated layer material, and which absorbs common odors.

It is also a feature and advantage of the invention to provide a personal care fabric or product which utilizes a treated water-permeable porous layer material that is more wettable and absorbs odors on at least one outer surface.

It is also a feature and advantage of the invention to provide a medical fabric or product which utilizes a treated water-permeable porous layer material that is more wettable and absorbs odors on at least one outer surface.

DEFINITIONS

The term "water-permeable porous layer material" refers to a material present in one or more layers, such as a film, nonwoven fabric, or open-celled foam, which is porous, and which is water-permeable due to the flow of water and other aqueous liquids, through the pores. The pores in the film or foam, or spaces between fibers or filaments in a nonwoven web, are large enough and frequent enough to permit leakage and flow of liquid water through the material. The term does not include films and other materials which block the transfer of water, or which permit the transfer only by molecular diffusion.

The term "nonwoven fabric or web" means a web having a structure of individual fibers or threads which are interlaid, but not in a regular or identifiable manner as in a knitted fabric. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91.)

The term "microfibers" means small diameter fibers having an average diameter not greater than about 75 microns, for example, having an average diameter of from about 1 micron to about 50 microns, or more particularly, microfibers may have an average diameter of from about 1 micron to about 30 microns. Another frequently used expression of fiber diameter is denier, which is defined as grams per 9000 meters of a fiber. For a fiber having circular cross-section, denier may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex," which is defined as the grams per kilometer of fiber. Tex may be calculated as denier/9.

The term "spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average diameters larger than about 7 microns, more particularly, between about 10 and 30 microns.

The term "meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than 10 microns in diameter, and are generally self bonding when deposited onto a collecting surface. Meltblown fibers used in the present invention are preferably substantially continuous in length.

The term "monocomponent" fiber refers to a fiber formed from one or more extruders using only one polymer. This is not meant to exclude fibers formed from one polymer to which small amounts of additives have been added for color, anti-static properties, lubrication, hydrophilicity, repellency, etc. These additives (e.g., titanium dioxide for color) are generally present in an amount less than 5 weight percent and more typically about 2 weight percent or less.

The term "coform" material refers to a product containing about 10–90% by weight of thermoplastic meltblown fibers and about 10–90% by weight of staple-length pulp fibers dispersed within the meltblown fiber matrix. More commonly, coform materials contain about 20–70% by weight thermoplastic meltblown fibers and about 30–80% by weight pulp fibers.

The term "film" refers to a thermoplastic film made using a film extrusion process, such as a cast film or blown film extrusion process.

The term "water-permeable porous film" includes films, such as thermoplastic polymer-containing films, which permit the flow of water through open or inter-connected pores. The term includes films rendered porous by puncturing or aperturing, and to films rendered porous by mixing polymer with filler, forming a film from the mixture, and stretching the film sufficiently to form liquid passages through the film.

The term "open-celled foam material" refers to a layer material made with the aid of a foaming process, in which the cells in the foam create open pores from one surface of the layer to the opposite surface. The term does not include foams which substantially block the flow of liquid water, such as closed-cell foam materials.

The term "polymer" includes, but is not limited to, homopolymers, copolymers, such as for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to isotactic, syndiotactic and atactic symmetries.

The term "bicomponent filaments or fibers" refers to fibers which have been formed from at least two polymers extruded from separate extruders but spun together to form one fiber. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another or may be a side-by-side arrangement or an "islands-in-the-sea" arrangement. Bicomponent fibers are taught in U.S. Pat. No. 5,108,820 to Kaneko et al., U.S. Pat. No. 5,336,552 to Strack et al., and U.S. Pat. No. 5,382,400 to Pike et al., each of which is incorporated herein in its entirety by reference. For two component fibers, the polymers may be present in ratios of 75/25, 50/50, 25/75 or any other desired ratios. Conventional additives, such as pigments and surfactants, may be incorporated into one or both polymer streams, or applied to the filament surfaces.

The term "pulp fibers" refers to fibers from natural sources such as woody and non-woody plants. Woody plants include, for example, deciduous and coniferous trees. Non-woody plants include, for instance, cotton, flax, esparto grass, milkweed, straw, jute hemp, and bagasse.

The term "average pulp fiber length" refers to a weighted average length of pulp determined using a Kajaani fiber analyzer Model No. FS-100 available from Kajaani Oy Electronics in Kajaani, Finland. Under the test procedure, a fiber sample is treated with a macerating liquid to ensure that no fiber bundles or shives are present. Each fiber sample is dispersed in hot water and diluted to about a 0.001% concentration. Individual test samples are drawn in approximately 50 to 500 ml portions from the dilute solution and tested using the standard Kajaani fiber analysis procedure. The weighted average fiber lengths may be expressed by the following equation:

$$\sum_{X_i>0}^{k} (X_i * n_i)/n$$

where
k=maximum fiber length,
$X_i$=individual fiber length,
$n_i$=number of fibers having length $X_i$ and
n=total number of fibers measured.

The term "superabsorbent material" refers to a water-swellable, water-insoluble organic or inorganic material capable, under the most favorable conditions, of absorbing at least about 20 times its weight, preferably at least about 30 times its weight in an aqueous solution containing 0.9% by weight sodium chloride.

The term "through-air bonding" or "TAB" means a process of bonding a nonwoven, for example, a bicomponent fiber web in which air which is sufficiently hot to melt one of the polymers of which the fibers of the web are made is forced through the web. The air velocity is often between 100 and 500 feet per minute and the dwell time may be as long as 6 seconds. The melting and resolidification of the polymer provides the bonding. Through-air bonding has restricted variability and is generally regarded as a second step bonding process. Since TAB requires the melting of at least one component to accomplish bonding, it is restricted to webs with two components such as bicomponent fiber webs or webs containing an adhesive fiber or powder.

The term "thermal point bonding" involves passing a fabric or web of fibers to be bonded between a heated calender roll and an anvil roll. The calender roll is usually, though not always, patterned in some way so that the entire fabric is not bonded across its entire surface. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen and Pennings or "EHP" bond pattern which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern which has a bond area of about 16.9%. The C-Star pattern has a cross-directional bar or "corduroy" design interrupted by shooting stars. Other common patterns include a diamond pattern with repeating and slightly offset diamonds and a wire weave pattern looking as the name suggests (e.g., like a window screen). Typically, the percent bonding area varies from around 10% to around 30% of the area of the fabric laminate web. As is well known in the art, the spot bonding holds the laminate layers together as well as imparts integrity to each individual layer by bonding filaments and/or fibers within each layer.

The term "personal care product" includes without limitation diapers, training pants, swim wear, absorbent underpants, baby wipes, adult incontinence products, and feminine hygiene products.

The term "medical product" includes without limitation garments, underpads, bandages, absorbent drapes, and medical wipes.

The term "hydrophilic" or "wettable" means that the polymeric material has an apparent surface free energy such that the polymeric material is wettable by an aqueous medium (i.e., a liquid medium of which water is a major component). That is, an aqueous medium wets the non-woven fabric. "Apparent surface free energy" refers to the highest surface tension of an aqueous liquid which wets the polymeric material. For example, the apparent surface free energy of a polymeric material that is wetted by an aqueous liquid having a surface tension of 72 dynes/cm, is at least 72 dynes/cm and possibly higher. In the fabrics of the invention, a surface of the nonwoven fabric has been treated with a surfactant-modified odor control agent using internal or external application techniques as described below.

The term "surfactant" refers to a compound or blend which, when applied to a surface of a substrate, causes the surface to become more "wettable" as defined above. In one instance, the substrate is not independently wettable and the surfactant causes it to become wettable. In another instance, the substrate is somewhat wettable and the surfactant causes it to become more wettable, or more easily wetted.

The term "surfactant-producing moiety" or "surfactant-producing compound" refers to a chemical group or compound which, when reacted or blended with another compound (e.g., an odor control agent) causes the reacted compound or blend to behave as a surfactant. The surfactant-producing moiety or compound may or may not behave as a surfactant prior to the chemical reaction or blending.

The term "odor control agent" includes compounds and blends which inhibit the formation of at least one undesirable odor, as well as compounds and blends which absorb an undesirable odor that has already formed.

The term "surfactant-modified odor control agent" refers to a blend, and/or a reaction product, between an odor control agent and a surfactant or surfactant-producing moiety, which acts as both a surfactant and an odor control agent.

DETAILED DESCRIPTION OF THE PRESENTLY PREFERRED EMBODIMENTS

The invention is a water-permeable layer material having at least one odor-reducing surface. The starting material for the invention is a water-permeable layer material. For instance, the starting material for the invention may be a porous thermoplastic layer or multilayer material capable of transmitting water (and other aqueous liquids) through the pores. Examples of suitable starting materials include thermoplastic nonwoven webs, open-celled foam layers, and thermoplastic polymer-containing films which are apertured or otherwise rendered porous, such as by stretching a film made from a mixture of a thermoplastic material and a particulate filler.

The starting material is treated with a surfactant-modified odor control agent. The surfactant-modified odor control agent is produced by blending a cyclodextrin-based odor control agent with a surfactant compound, and/or by chemically reacting a cyclodextrin-based odor control agent with a surfactant-producing compound. The surfactant-modified odor control agent is applied to the starting material using conventional techniques for applying surfactants externally or internally. Preferably, the surfactant-modified odor control agent is applied externally in the form of a liquid, using techniques such as dipping, spraying, brushing, or other liquid coating techniques. The surfactant-modified odor control agent may be blended with water or another solvent to facilitate its application.

The preferred starting material for the invention is a nonwoven web including a plurality of filaments made from one or more polymers. The nonwoven web may be a spunbond web, a meltblown web, a bonded carded web, or another type of nonwoven web, and may be present in a single layer or a multilayer composite including one or more nonwoven web layers and, in some instances, one or more film or foam layers. The web may include monocomponent or bicomponent filaments, or a combination including one or both filament types. The nonwoven web may have a variety of basis weights, preferably ranging from about 0.1–200 grams per square meter (gsm). One preferred nonwoven web is a coform material, which includes a matrix of polyolefin meltblown fibers and a large percentage (often 30–80% by weight) of pulp fibers dispersed in the matrix of the meltblown fibers. Another preferred nonwoven web is an airlaid web of polyolefin fibers and pulp fibers.

A wide variety of thermoplastic polymers may be used to construct the starting porous layer material, including without limitation polyamides, polyesters, polyolefins, copolymers of ethylene and propylene, copolymers of ethylene or propylene with a $C_4$–$C_{20}$ alpha-olefin, terpolymers of ethylene with propylene and a $C_4$–$C_{20}$ alpha-olefin, ethylene vinyl acetate copolymers, propylene vinyl acetate copolymers, styrene-poly(ethylene-alpha-olefin) elastomers, polyurethanes, A–B block copolymers where A is formed of poly(vinyl arene) moieties such as polystyrene and B is an elastomeric midblock such as a conjugated diene or lower alkene, polyethers, polyether esters, polyacrylates, ethylene alkyl acrylates, polyisobutylene, poly-1-butene, copolymers of poly-1-butene including ethylene-1-butene copolymers, polybutadiene, isobutylene-isoprene copolymers, and combinations of any of the foregoing. Polyolefins are preferred. Polyethylene and polypropylene homopolymers and copolymers are most preferred.

The odor control agent, which can be mixed or chemically reacted with a surfactant to make the surfactant-modified odor control agent, includes a compound selected from cyclodextrins. Suitable cyclodextrins include any of the known cyclodextrins containing from six to twelve glucose units, including without limitation alpha-cyclodextrins (6 glucose units arranged in a ring), beta-cyclodextrins (7 glucose units arranged in a ring), and gamma-cyclodextrins (8 glucose units arranged in a ring). The coupling and configuration of the glucose units causes the cyclodextrins to have a conical molecular structure with a hollow interior lined by hydrogen atoms and glycosidic bridging oxygen atoms. When the cyclodextrins alone are applied to the starting substrate material, the material does not have sufficient wettability to aqueous liquids.

In accordance with the invention, the precursor odor control agent is mixed with a surfactant, and/or chemically reacted with a surfactant-producing compound, to yield the surfactant-modified odor control agent which can serve both functions. As indicated above, the term "surfactant-producing compound" includes surfactants, and other compounds which behave as surfactants following the chemical reaction. The surfactant and/or surfactant-producing compound should include at least one functional group which is compatible with the thermoplastic polymer used to make the fibrous nonwoven web. Suitable functional groups include alkyl groups having about 3–20 carbon atoms, including without limitation propyl, benzyl, isopropyl, butyl, tertiary butyl, allyl, alkyl-benzyl, hexyl, octyl, decyl, lauryl, myristyl, palmityl, cocyl, oleyl, stearyl, and other common alkyl groups. Alkyl groups can be combined with cyclodextrins by mixing an alkyl-containing surfactant with a cyclodextrin odor control agent (e.g., in a solvent such as water), or by reacting a hydroxyl group on the cyclodextrin under appropriate conditions with a surfactant-producing alkyl compound such as an alkyl-containing surfactant, an alkyl halide, an alkylating alkyl sulfate reactant, or another suitable alkylating compound. The mixing and/or chemical reaction can be accomplished using conventional techniques.

Other suitable functional groups include acyl groups having about 3–20 carbon atoms, including without limitation propionyl, butyryl, trifluoroacetyl, benzoyl, caproyl, caprylyl, capryl, lauroyl, myristoyl, palmitoyl, stearoyl, cocoyl, oleoyl, and other common acyl groups. Acyl groups can be combined with cyclodextrins by mixing an acyl-containing surfactant with a cyclodextrin odor-control agent (e.g., using a solvent such as water). Acyl groups can also be formed on cyclodextrins by reacting a hydroxyl group on the cyclodextrin under appropriate conditions with a surfactant-producing acyl compound such as an acyl-containing surfactant, acid anhydride, acid chloride, or another suitable acylating compound. The mixing and/or chemical reaction can be accomplished using conventional techniques.

Other suitable functional groups include those containing an aliphatic hydrocarbon group or derivative thereof which can be blended or reacted with a cyclodextrin to render it surface active. Suitable aliphatic hydrocarbon compounds include compounds containing the 2-ethylhexylglycidyl group, which can be mixed with a cyclodextrin, and/or attached to a cyclodextrin to form an ether, ester, or other derivative compound. Other suitable functional groups can also be employed, including suitable perfluoro and siloxane groups and compounds containing them. Examples include compounds containing the following groups:

where x=2 to 11,

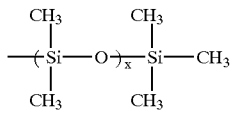

where x=2 to 20, and

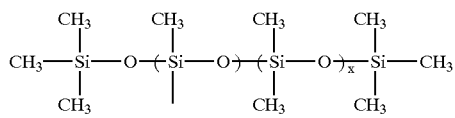

where x=2 to 20.

The resulting surfactant-modified odor control agent may be applied using internal or external application techniques known in the art. Some compounds and blends operate more favorably when applied internally and are called "internal additives." Others operate more favorably when applied externally and are called "external additives." Still other compounds and blends operate suitably as both internal and external additives.

As is generally known, an internal additive is typically blended with the polymer used to make the porous film, nonwoven web, or other porous thermoplastic layer material, and migrates to the surfaces of the porous film, nonwoven web filaments or other layer material during and/or after their formation. Often, the migration results from a stimulus, such as heat applied to the thermoplastic material. An external additive is applied externally to the surfaces of the layer material after it is formed. An external additive may be applied by dipping, soaking, spraying, or otherwise coating the porous thermoplastic layer material with a solvent or other medium containing the additive.

External application methods are presently preferred for the surfactant-modified odor control agents used with the treated materials of the invention. The surfactant-modified odor control agent (whether formed by blending or chemical reaction) may be mixed with water or another suitable solvent in a concentration of about 0.1–30% of the agent, preferably about 0.5–15% by weight of the agent, more preferably about 1–5% by weight of the agent. The solution may then be applied to a porous, water-permeable thermoplastic substrate by immersion, spraying, brush coating, printing, or another suitable technique. The treated layer material can then be dried using heat, forced air convection, vacuum-induced evaporation, or another conventional drying technique.

The treated layer materials thus formed have wettability to aqueous liquids, and odor resistance to a wide variety of odor-producing compounds. The terms "odor resistance" and "odor control" refer to the ability of the treated materials to react with, neutralize, form complexes with, or otherwise reduce or eliminate the odors produced by these compounds.

Examples of odor-producing compounds which the treated layer materials of the invention may reduce or eliminate, include without limitation ammonia, triethylamine, isovaleric acid, dimethyldisulfide, dimethyltrisulfide, indole, skatole, and the like.

The amount of surfactant-modified odor control agent needed to provide sufficient wetting and odor absorption may vary depending on the surfactant-producing compound and odor control agent blended or reacted together, the base polymer type, and whether the surfactant-modified odor control agent is added internally or externally. On a solvent-free weight basis, the surfactant-modified odor control agent should generally constitute about 0.1–10% by weight of the porous, water-permeable substrate layer to which it is applied, preferably about 0.5–8% by weight, more preferably about 2–7% by weight.

The treated water-permeable layer materials thus formed can be used in a wide variety of absorbent product applications including, in particular, personal care absorbent products. Personal care absorbent products include diapers, training pants, swim wear, absorbent underpants, baby wipes, adult incontinence products, feminine hygiene products, and the like. In most absorbent products, the treated water-permeable layer material is used as a cover sheet or containment matrix for an absorbent medium capable of absorbing aqueous liquids. An absorbent medium may include, for instance, pulp fibers alone or in combination with a superabsorbent material. The treated water-permeable layer material can also be used in medical absorbent products, including without limitation garments, underpads, absorbent drapes, bandages, and medical wipes.

The pulp fibers may be any high-average fiber length pulp, low-average fiber length pulp, or mixtures of the same. Preferred pulp fibers include cellulose fibers. The term "high average fiber length pulp" refers to pulp that contains a relatively small amount of short fibers and non-fiber particles. High fiber length pulps typically have an average fiber length greater than about 1.5 mm, preferably about 1.5–6 mm, as determined by an optical fiber analyzer, such as the Kajaani tester referenced above. Sources generally include non-secondary (virgin) fibers as well as secondary fiber pulp which has been screened. Examples of high average fiber length pulps include bleached and unbleached virgin softwood fiber pulps.

The term "low average fiber length pulp" refers to pulp that contains a significant amount of short fibers and non-fiber particles. Low average fiber length pulps have an average fiber length less than about 1.5 mm, preferably about 0.7–1.2 mm, as determined by an optical fiber analyzer such as the Kajaani tester referenced above. Examples of low fiber length pulps include virgin hardwood pulp, as well as secondary fiber pulp from sources such as office waste, newsprint, and paperboard scrap.

Examples of high average fiber length wood pulps include those available from the U.S. Alliance Coosa Pines Corporation under the trade designations Longlac 19, Coosa River 56, and Coosa River 57. The low average fiber length pulps may include certain virgin hardwood pulp and secondary (i.e., recycled) fiber pulp from sources including newsprint, reclaimed paperboard, and office waste. Mixtures of high average fiber length and low average fiber length pulps may contain a predominance of low average fiber length pulps. For example, mixtures may contain more than about 50% by weight low-average fiber length pulp and less than about 50% by weight high-average fiber length pulp.

The term "superabsorbent" or "superabsorbent material" refers to a water swellable, water-insoluble organic or inorganic material capable, under the most favorable conditions, of absorbing at least about 20 times its weight and, more desirably, at least about 30 times its weight in an aqueous solution containing 0.9 weight percent sodium chloride.

The superabsorbent materials can be natural, synthetic and modified natural polymers and materials. In addition, the superabsorbent materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic superabsorbent material polymers include the alkali metal and ammonium salts of poly(acrylic acid) and poly(methacrylic acid), poly(acrylamides), poly (vinyl ethers), maleic anhydride copolymers with vinyl ethers and alpha-olefins, poly(vinyl pyrrolidone), poly (vinylmorpholinone), poly(vinyl alcohol), and mixtures and copolymers thereof. Further superabsorbent materials include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic super-absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Superabsorbent materials may be xerogels which form hydrogels when wetted. The term "hydrogel," however, has commonly been used to also refer to both the wetted and unwetted forms of the superabsorbent polymer material. The superabsorbent materials can be in many forms such as flakes, powders, particulates, fibers, continuous fibers, networks, solution spun filaments and webs. The particles can be of any desired shape, for example, spiral or semi-spiral, cubic, rod-like, polyhedral, etc. Needles, flakes, fibers, and combinations may also be used.

Superabsorbents are generally available in particle sizes ranging from about 20 to about 1000 microns. Examples of commercially available particulate superabsorbents include SANWET® IM 3900 and SANWET® IM-5000P, available from Hoescht Celanese located in Portsmouth, Va., DRYTECH® 2035LD available from Dow Chemical Co. located in Midland, Mich., and FAVOR® SXM880, available from Stockhausen, located in Greensboro, N.C. An example of a fibrous superabsorbent is OASIS® 101, available from Technical Absorbents, located in Grimsby, United Kingdom.

As indicated above, the treated water-permeable layer material may be a cover sheet or a matrix for an absorbent medium. Nonwoven filaments may be employed as a matrix, and may be combined with pulp fibers and (optionally) a superabsorbent material using processes well known in the art. For example, a coform process may be employed, in which at least one meltblown diehead is arranged near a chute through which other materials are added while the web is forming. Coform processes are described in U.S. Pat. No. 4,818,464 to Lau and U.S. Pat. No. 4,100,324 to Anderson et al., the disclosures of which are incorporated by reference. Thermoplastic nonwoven filaments and pulp fibers may also be combined using hydraulic entangling or mechanical entangling. A hydraulic entangling process is described in U.S. Pat. No. 3,485,706 to Evans, the disclosure of which is incorporated by reference.

When treated thermoplastic nonwoven filaments are used as a matrix for an absorbent nonwoven web composite, the composite should contain about 5–97% by weight pulp fibers, preferably about 35–95% by weight pulp fibers, more preferably about 50–95% by weight pulp fibers. When a superabsorbent material is present, it should constitute about 5–90% by weight of the composite, preferably about 10–60% by weight, more preferably about 20–50% by weight. In either case, the thermoplastic nonwoven filament matrix should constitute about 3–95% by weight of the composite, preferably about 5–65% by weight, more preferably about 5–50% by weight.

After combining the ingredients together, the absorbent nonwoven composites may be bonded together using the thermal point bonding or through-air bonding techniques described above, to provide a coherent high integrity structure.

The following samples were prepared and tested for wettability to water and for odor absorption properties.

EXAMPLE 1

A coform nonwoven fabric was prepared with 30% by weight meltblown polypropylene fibers and 70% by weight pulp fibers. The fabric had a basis weight of 170 grams/square meter. The coform fabric was not wettable to deionized water.

EXAMPLE 2

The coform fabric described as Example 1 was treated with 1.0 wt % beta-cyclodextrin (Cerestar USA, Inc.) as follows. Three grams of beta-cyclodextrin were dissolved in deionized water, and the solution was diluted with deionized water to a total weight of 750 grams. The surface tension of this 0.4 wt % beta-cyclodextrin solution was measured at 74.6 dynes/cm, about the same as pure deionized water (75.2 dynes/cm). The beta-cyclodextrin could not be applied to the coform fabric from this solution because the solution would not wet out the fabric due to the high surface tension. Therefore, 3.8 grams of hexanol was added to the solution to give 0.4 wt % beta-cyclodextrin/0.5 wt % hexanol/99.1 wt % deionized water. The surface tension of this new solution was measured at 36 dynes/cm, low enough to wet out the coform fabric and apply the beta-cyclodextrin treatment to the surface of the fabric. The coform fabric was soaked in the solution for about 1 minute, squeezed with a nip to remove excess solution, and dried in a hood. This procedure gave an add-on level of 1.0 wt % beta-cyclodextrin, which was determined from the wet pickup of the fabric and the solution concentration, calculated as follows: wt % of treatment=[(wet wt of fabric minus dry wt of fabric), divided by dry wt of fabric], multiplied by wt % of treatment in the solution. The dried fabric with 1.0 wt % beta cyclodextrin treatment was tested for wettability to deionized water. The fabric was only slightly wettable to the water, and therefore, would not be preferred for use in a personal care product, which must absorb liquids.

EXAMPLE 3

The coform fabric described as Example 1 was treated with 1.0 wt % 2-ethylhexylglycidyl ether beta-cyclodextrin (EHGE Beta-CD) as follows. Three grams of EHGE Beta-CD (Cerestar USA, Inc.) was mixed with 750 grams of deionized water. This mixture was heated to about 60° C. over a 1 to 2 hour time period in order to disperse and dissolve the EHGE Beta-CD. This 0.4 wt % EHGE Beta-CD/deionized water solution was cooled to less than 30° C. before being used to soak the coform fabric. The surface tension of the solution was measured at 34 dynes/cm, low enough to easily wet out the coform fabric without the need for hexanol. The coform fabric was soaked in the 0.4 wt % EHGE Beta-CD solution for about 1 minute, squeezed with a nip to remove excess solution, and dried in a hood. The percent treatment add-on for the fabric was determined to be 1.0 wt % EHGE Beta-CD, using the procedure described for Sample 2. The dried EHGE Beta-CD treated coform fabric was tested for wettability to deionized water. The fabric was highly wettable to the water, as drops of water completely penetrated the fabric in less than 1 second. Therefore, the EHGE Beta-CD-treated coform fabric would be preferred for use in a personal care product as both wettability to fluids and odor absorption properties are provided.

The results for these samples clearly show the benefit of using surfactant-modified cyclodextrins as treatments for water permeable porous layer materials. These treatments provide the materials with both wettability to fluids and odor absorbing properties.

While the embodiments of the invention described herein are presently preferred, various modifications and improvements can be made without departing from the spirit and scope of the invention. The scope of the invention is indicated by the appended claims, and all changes that fall within the meaning and range of equivalents are intended to be embraced therein.

We claim:

1. A treated water-permeable layer material comprising a porous, thermoplastic water-permeable substrate layer treated with a surfactant-modified odor control agent produced by chemically reacting a surfactant-producing compound with a cyclodextrin odor-control agent.

2. The treated water-permeable layer material of claim 1, wherein the substrate layer comprises a thermoplastic nonwoven filament web.

3. The treated water-permeable layer material of claim 1, wherein the substrate layer comprises a porous film.

4. The treated water-permeable layer material of claim 1, wherein the substrate comprises an open-celled foam layer.

5. The treated water-permeable layer material of claim 1, wherein the cyclodextrin odor control agent comprises a compound selected from alpha-cyclodextrins, beta-cyclodextrins, gamma cyclodextrins, and combinations thereof.

6. The treated water-permeable layer material of claim 5, wherein the cyclodextrin odor control agent comprises a beta-cyclodextrin.

7. The treated water-permeable layer material of claim 5, wherein the cyclodextrin odor control agent comprises an alpha-cyclodextrin.

8. The treated water-permeable layer material of claim 5, wherein the cyclodextrin odor control agent comprises a gamma cyclodextrin.

9. The treated water-permeable layer material of claim 1, wherein the surfactant or surfactant-producing compound comprises an alkyl group.

10. The treated water-permeable layer material of claim 9, wherein the alkyl group comprises about 3–20 carbon atoms.

11. The treated water-permeable layer material of claim 1, wherein the surfactant or surfactant-producing compound comprises an acyl group.

12. The treated water-permeable layer material of claim 11, wherein the acyl group comprises about 3–20 carbon atoms.

13. The treated water-permeable layer material of claim 1, wherein the surfactant or surfactant producing compound comprises an aliphatic hydrocarbon group.

14. The treated water-permeable layer material of claim 13, wherein the aliphatic hydrocarbon group comprises a 2-ethylhexylglycidyl group.

15. The treated water-permeable layer material of claim 1, wherein the surfactant or surfactant-producing compound comprises a perfluoro group.

16. The treated water permeable layer material of claim 1, wherein the surfactant or surfactant-producing compound comprises a siloxane group.

17. The treated water-permeable layer material of claim 1, wherein the surfactant-modified odor control agent is applied externally.

18. The treated water-permeable layer material of claim 1, wherein the surfactant-modified odor control agent is applied internally.

19. The treated water-permeable layer material of claim 1, comprising about 0.05–10% by weight of the surfactant-modified odor control agent.

20. The treated water-permeable layer material of claim 1, comprising about 0.1–5% by weight of the surfactant-modified odor control agent.

21. The treated water-permeable layer material of claim 1, comprising about 1–3% by weight of the surfactant-modified odor control agent.

22. The treated water-permeable layer material of claim 1, wherein the layer material comprises a polymer selected from the group consisting of polyamides, polyolefins, polyesters, copolymers of ethylene and propylene, copolymers of ethylene or propylene with a $C_4$–$C_{20}$ alpha-olefin, terpolymers of ethylene with propylene and a $C_4$–$C_{20}$ alpha-olefin, ethylene vinyl acetate copolymers, propylene vinyl acetate copolymers, styrene-poly(ethylene-alpha-olefin) elastomers, polyurethanes, A–B block copolymers where A is formed of poly(vinyl arene) moieties such as polystyrene and B is an elastomeric midblock such as a conjugated diene or lower alkene, polyethers, polyether esters, polyacrylates, ethylene alkyl acrylates, polyisobutylene, polybutadiene, isobutylene-isoprene copolymers, and combinations of any of the foregoing.

23. The treated water-permeable layer material of claim 1, wherein the layer material comprises a polyolefin.

24. The treated water-permeable layer material of claim 1, wherein the layer material comprises a polyethylene homopolymer or copolymer.

25. The treated water-permeable layer material of claim 1, wherein the layer material comprises a polypropylene homopolymer or copolymer.

26. A treated water-permeable layer material comprising a thermoplastic nonwoven filament web treated with a surfactant-modified cyclodextrin, produced by chemically reacting a surfactant-producing compound with a cyclodextrin odor-control agent;

the treated nonwoven web having better wettability and odor control than the nonwoven web without the surfactant-modified cyclodextrin;

wherein the odor comprises a malodor selected from ammonia, triethylamine, isovaleric acid, dimethyldisulfide, dimethyltrisulfide, indole, skatole, and combinations thereof.

27. The treated water-permeable layer material of claim 26, wherein the surfactant-modified cyclodextrin comprises a cyclodextrin reacted or blended with an alkyl compound.

28. The treated water-permeable layer material of claim 26, wherein the surfactant-modified cyclodextrin comprises a cyclodextrin reacted or blended with an acyl compound.

29. The treated water-permeable material of claim 26, wherein the surfactant-modified cyclodextrin comprises a cyclodextrin reacted or blended with an aliphatic hydrocarbon.

30. The treated nonwoven fabric of claim 29, wherein the aliphatic hydrocarbon comprises 2-ethylhexylglycidyl ether.

31. An absorbent product, comprising:
    an absorbent medium capable of absorbing aqueous liquids; and
    a thermoplastic water-permeable layer material having a treated surface capable of reducing at least one odor selected from ammonia, triethylamine, isovaleric acid, dimethyldisulfide, dimethyltrisulfide, indole, skatole, and combinations thereof;
    wherein the treated surface comprises a surfactant-modified cyclodextrin compound, produced by chemically reacting a surfactant-producing compound with a cyclodextrin odor-control agent.

32. The absorbent product of claim 31, comprising a diaper.

33. The absorbent product of claim 31, comprising training pants.

34. The absorbent product of claim 31, comprising swim wear.

35. The absorbent product of claim 31, comprising absorbent underpants.

36. The absorbent product of claim 31, comprising a baby wipe.

37. The absorbent product of claim 31, comprising an adult incontinence product.

38. The absorbent product of claim 31, comprising a feminine hygiene product.

39. The absorbent product of claim 31, comprising a medical garment.

40. The absorbent product of claim 31, comprising an underpad.

41. The absorbent product of claim 31, comprising an absorbent drape.

42. The absorbent product of claim 31, comprising a bandage.

43. The absorbent product of claim 31, comprising a medical wipe.

* * * * *